United States Patent [19]

Yamauchi et al.

[11] Patent Number: 5,008,260
[45] Date of Patent: Apr. 16, 1991

[54] CEPHEM DERIVATIVES

[75] Inventors: Hiroshi Yamauchi; Isao Sugiyama; Isao Saito; Seiichiro Nomoto; Takashi Kamiya; Yoshimasa Machida; Shigeto Negi, all of Ibaraki, Japan

[73] Assignee: Eisai Co., Ltd., Tokyo, Japan

[21] Appl. No.: 167,153

[22] Filed: Mar. 16, 1988

Related U.S. Application Data

[62] Division of Ser. No. 818,824, Jan. 14, 1986, Pat. No. 4,748,171.

[30] Foreign Application Priority Data

Jan. 14, 1985 [JP] Japan .................................. 60-3181
Apr. 11, 1985 [JP] Japan .................................. 60-75333
Aug. 9, 1985 [JP] Japan .................................. 60-174326

[51] Int. Cl.$^5$ .................. C07D 501/38; A61K 31/545
[52] U.S. Cl. .................................... 514/202; 540/222; 540/225
[58] Field of Search ................ 514/202; 540/222, 225, 540/221

[56] References Cited

U.S. PATENT DOCUMENTS

| | | | |
|---|---|---|---|
| 4,525,473 | 6/1985 | Aluraki et al. ........................ | 514/202 |
| 4,698,336 | 10/1987 | Saito et al. ........................... | 540/222 |
| 4,748,171 | 5/1988 | Yamauchi et al. ................... | 540/222 |
| 4,929,612 | 5/1990 | Machida et al. ..................... | 540/222 |

FOREIGN PATENT DOCUMENTS 0062321 10/1982 European Pat. Off. ............. 544/22
03938 9/1985 PCT Int'l Appl. ................... 544/22

Primary Examiner—Nicholas S. Rizzo
Attorney, Agent, or Firm—Wenderoth, Lind & Ponack

[57] ABSTRACT

Described herein is a cephem derivative represented by the general formula:

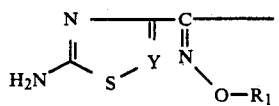

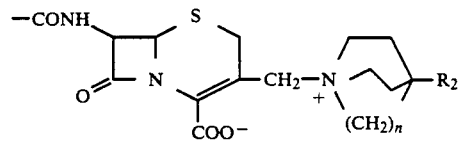

wherein n stands for 1 or 2, Y stands for CH or nitrogen atom, $R_1$ represents a lower hydrocarbon group or a carboxyl-substituted, a carbamoyl-substituted, or a cyclopropyl-substituted lower alkyl group, and $R_2$ denotes hydroxyl group, a lower alkyl group, a hydroxy-substituted lower alkyl group, or carbamoyl group. The derivative is useful as an antibacterial agent. Also described herein are processes for the production of the derivative, antibacterial composition, intermediate of the derivative and process for the production thereof.

10 Claims, No Drawings

CEPHEM DERIVATIVES

This application is a division of Ser. No. 818,824 filed Jan. 14, 1986, now U.S. Pat. No. 4,748,171.

BACKGROUND OF THE INVENTION

1. Field of the Invention

This invention relates to novel cephem derivatives useful as antibacterial agents, process for the production thereof, antibacterial composition, intermediates thereof and process therefor.

2. Description of the Prior Art

A number of compounds have heretofore been known which contain a substituted thiadiazolylacetamido group or substituted thiazolylacetamido group at the 7-position of the cephem skeleton. For example, the compounds may be disclosed in the following publications: Japanese Patent Application Laid-open Nos. 11600/1980, 105689/1980, 24389/1982, 81493/1982, 4789/1983, 41887/1983, 59992/1983, 149296/1981, 102293/1977, 116492/1977, 125190/1977, 154786/1979, 192394/1982, 219292/1984, 97982/1985, 197693/1985, 231683/85, etc.

Particularly, 7β-[(Z)-2-(2-aminothiazol-4-yl)-2-methoxyiminoacetamido]-3-(1-quinuclidinio)methyl-3-cephem-4-carboxylate is described in Japanese Patent Application Laid-open Nos. 219292/1984, 197693/1985, and 231683/1985. However, this compound can not be practically used from a clinical point of view, because its acute toxic value [$LD_{50}$ (mouse, intravenous injection)] amounts to about 100 mg/kg or less, and hence, the compound is very toxic.

SUMMARY OF THE INVENTION

The present inventors have found that cephem derivatives, each of which has the hereinunderdescribed group at the 3-position of the cephem skeleton, have excellent antibacterial activities, leading to completion of this invention:

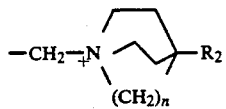

wherein n stands for 1 or 2 and $R_2$ denotes hydroxyl group, a lower alkyl, a hydroxy-substituted lower alkyl group, or carbamoyl group.

An object of this invention is therefore to provide novel compounds useful as antibacterial agents, their production process and their use as an antibacterial composition.

Further object of this invention is to provide novel intermediates of the above cephem derivatives and the process for the production thereof.

DESCRIPTION OF THE INVENTION

The compounds of this invention are defined as follows:

A cephem derivative represented by the general formula:

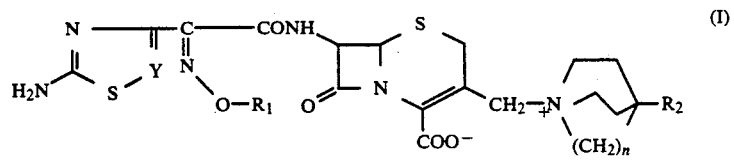

wherein n stands for 1 or 2, Y stands for CH or nitrogen atom, $R_1$ represents a lower hydrocarbon group or a carboxyl-substituted, a carbamoyl-substituted, or a cyclopropyl-substituted lower alkyl group, and $R_2$ denotes hydroxyl group, a lower alkyl group, a hydroxy-substituted lower alkyl group, or carbamoyl group, or a pharmaceutically acceptable salt thereof.

As the lower hydrocarbon group represented by $R_1$ in the general formula (I), there may be mentioned lower alkyl groups such as methyl, ethyl, n-propyl, i-propyl, n-butyl, t-butyl and sec-butyl; lower alkenyl groups such as vinyl and allyl; lower alkynyl groups such as propargyl; and the like. Examples of the carboxy-substituted lower alkyl group represented by $R_1$ may include carboxymethyl, 2-carboxy-ethyl, 3-carboxypropyl, 1-carboxyethyl, 1-carboxy-1-methylethyl, and the like. Exemplary carbamoyl-substituted lower alkyl groups represented by $R_1$ may include carbamoylmethyl, 2-carbamoylethyl, 3-carbamoylpropyl, 1-carbamoyl-1-methylethyl, 1-carbamoylethyl and the like. Exemplary cyclopropyl-substituted lower alkyl groups represented by $R_1$ may include cyclopropylmethyl, 2-cyclopropylethyl, and the like.

As exemplary hydroxy-substituted lower alkyl groups represented by $R_2$, there may be mentioned hydroxymethyl, 2-hydroxyethyl, 1-hydroxyethyl, 3-hydroxypropyl and the like. Exemplary lower alkyl groups represented by $R_2$ may include methyl, ethyl, n-propyl, i-propyl, n-butyl, t-butyl, and the like.

As non-toxic salts of the compounds of the general formula (I), may be mentioned their pharmaceutically-acceptable salts, for example, alkali metal salts such as sodium salts and potassium salts; alkaline earth metal salts such as calcium salts and magnesium salts; inorganic acid salts such as hydrochlorides, hydrobromides, hydroiodides, sulfates, carbonates and bicarbonates; organic carboxylates such as maleates, lactates and tartrates; organic sulfonates such as methanesulfonates, benzenesulfonates and toluenesulfonates; amino acid salts such as arginine salts, lysine salts, serine salts, aspartates and glutamates; amine salts such as trimethylamine salts, triethylamine salts, pyridine salts, procaine salts, picoline salts, dicyclohexylamine salts, N,N'-dibenzylethylenediamine salts, N-methylglucamine salts, diethanolamine salts, triethanolamine salts, tris(hydroxymethylamino)methane salts and phenethylbenzylamine salts; and the like.

Each of the compounds of the general formula (I), which pertains to the present invention, has its syn-isomer (Z) and anti-isomer (E) with respect to its configuration at the following moiety:

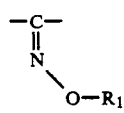

Although both isomers are included in the present invention, the syn-isomers are desired owing to their anti-bacterial activities.

The compounds of this invention can be produced by the following processes.

I: First Process for the Production

The compounds of the general formula (I) and their pharmaceutically acceptable salts can be obtained by reacting a compound represented by the general formula:

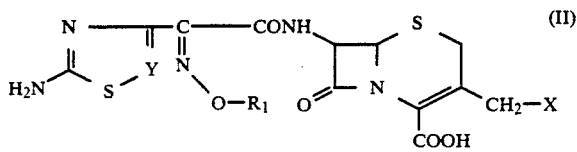

wherein Y and $R_1$ have the same meanings as defined above and X represents a halogen atom, or a compound wherein the amino group and/or carboxyl group is/are protected by a protective group, or a salt thereof, with a compound represented by the general formula:

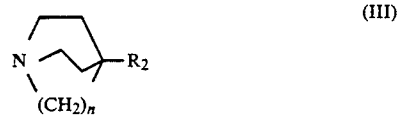

wherein n and $R_2$ have the same meanings as defined above, or with a salt thereof, followed by optionally removing the protective group.

As halogen atoms represented by X in the above general formula (II), there may be mentioned iodine atom, bromine atom and chlorine atom. Of these, iodine atom and bromine atom are particularly desired.

The above reaction may be carried out at a reaction temperature of $-10°$ C. to $60°$ C. or preferably $0°$ C. to $40°$ C. As a reaction solvent, an anhydrous organic solvent is desired. As usable organic solvents, there may be mentioned lower alkylnitriles such as acetonitrile and propionitrile; halogenated lower alkyls such as chloromethane, methylene chloride and chloroform; ethers such as tetrahydrofuran and dioxane; amides such as N,N-dimethylformamide; esters such as ethyl acetate; ketones such as acetone; and hydrocarbons such as benzene; as well as mixed solvents thereof.

As the salts of the compounds of the general formulae (II) and (III) and the protective groups for the amino group and carboxyl group in the compounds of the general formula (II), those employed routinely may also be used so long as they do not impair the reaction.

For example, the formyl group, acetyl group, chloroacetyl group, dichloroacetyl group, t-butoxycarbonyl group, benzyloxycarbonyl group, trityl group, p-methoxybenzyl group, diphenylmethyl group and the like may be used as protective groups for amino group; and p-methoxybenzyl group, p-nitrobenzyl group, t-butyl group, methyl group, 2,2,2-trichloroethyl group, diphenylmethyl group, pivaloyloxymethyl group and the like as protective groups for carboxyl group. Further, use of a silylating agent such as bis(trimethylsilyl)acetamide, N-methyl-N-(trimethylsilyl)acetamide or N-methyl-N-trimethylsilyltrifluoroacetamide and the like is convenient because such a silylating agent can protect both amino and carboxyl groups at the same time.

As salts of the compounds of the general formulae (II) and (III), suitable selection may be made from their salts such as their alkali metal salts such as sodium salts and potassium salts; alkaline earth metal salts such as calcium salts and magnesium salts; ammonium salts; inorganic acid salts such as hydrochlorides, hydrobromides, sulfates, carbonates, hydroiodides and bicarbonates; organic carboxylates such as acetates, maleates, lactates and tartrates; organic sulfonates such as methanesulfonates, benzenesulfonates and toluenesulfonates; amine salts such as trimethylamine salts, triethylamine salts, pyridine salts, procaine salts, picoline salts, dicyclohexylamine salts, N,N'-dibenzylethylenediamine salts, N-methylglucamine salts, diethanolamine salts, triethanolamine salts, tris(hydroxymethylamino)methane salts and phenethylbenzylamine salts; amino acid salts such as arginine salts, aspartates, lysine salts, glutamates and serine salts; and the like.

The removal of the protective group can be carried out by any conventional processes such as hydrolysis, reduction, and the like, depending on the types of the protective groups used.

II: Second Process for Production

The compounds of the general formula (I) and their pharmaceutically acceptable salts can also be obtained by reacting a compound represented by the general formula:

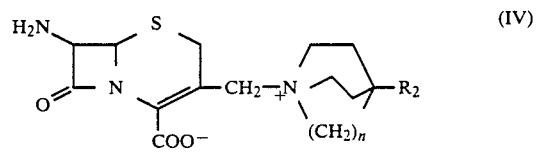

wherein n and $R_2$ have the same meanings as defined above, or a compound wherein the group $—COO^-$ has been protected by a protective group, or a salt thereof, with a compound represented by the general formula:

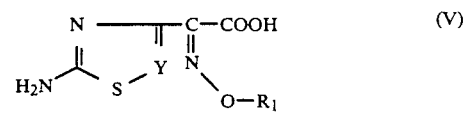

wherein Y and $R_1$ have the same meanings as defined above, or a compound wherein the amino group has been protected by a protective group, or a reactive derivative at the carboxyl group thereof, or a salt thereof, and followed by optionally removing the protective group.

The process may be carried out in accordance with any conventional N-acylating reaction conditions. For example, the reaction may be performed in an inert solvent at a temperature of $-50°$ C. to $50°$ C., preferably $-20°$ C. to $30°$ C. in the presence or absence of a base. Examples of the inert solvent include acetone, tetrahydrofuran, N,N-dimethylformamide, N,N-dimethylacetamide, dioxane, dichloromethane, chloroform, benzene, toluene, acetonitrile, or the mixed solvents thereof. Examples of the base include N,N-dimethylaniline, triethylamine, pyridine, N-methylmorpholine and the like.

In the case where the carboxylic acids (—COOH) represented by the general formula (V) are used in the process according to the present invention, the reaction is preferably carried out in the presence of a condensation agent such as N,N'-dicyclohexylcarbodiimide, N,N'-diethylcarbodiimide, N-cyclohexyl-N'-morpholinoethylcarbodiimide, trialkyl phosphite, ethyl polyphosphate, p-toluenesulfonic acid chloride and the like. Furthermore, in the case where such a reactive derivative at the carboxyl group in the general formula (V) is used, an example of the reactive derivative includes acid halides such as acid chloride, acid bromide and the like; symmetrical acid anhydrides; mixed acid anhydrides with carboxylic acid such as ethyl chlorocarbonate, trimethylacetic acid, thioacetic acid, diphenylacetic acid and the like; active esters with 2-mercaptopyridine, cyanomethanol, p-nitrophenol, 2,4-dinitrophenol, pentachlorophenol and the like; and active acid amides with saccharin and the like.

As the protective groups for —COO⁻ of the compound of the general formula (IV), there can be similarly used the groups which were mentioned as the protective groups for carboxyl group of the compound of the aforesaid general formula (II).

As the protective group for the amino group of the compound of the general formula (V), there can be used the groups which were illustrated as the protective groups for the amino group of the compound of the above-mentioned general formula (II).

These protective groups can be removed by any conventional manner, such as hydrolysis, reduction, and the like, depending on the types of the protective groups used.

As the salts of the compounds of the formulae (IV) and (V), there may be suitably selected the salts which were illustrated as the salts of the compounds of the general formulae (II) and (III).

The novel compounds represented by the general formula:

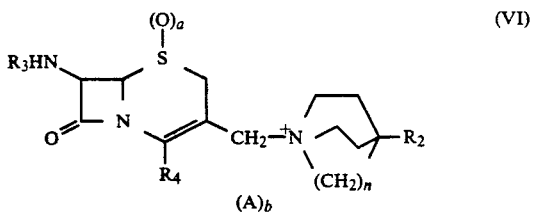

wherein n and $R_2$ have the same meanings as defined above, a is 0 or 1, $R_3$ represents hydrogen atom or a protective group for the amino group, A denotes an anion, and b stands for 0, when $R_4$ denotes a group —COO⁻, and for 1, when $R_4$ represents a group —COOR$_5$ ($R_5$ being a protective group for the carboxyl group), or a salt thereof, inclusive of the compounds represented by the general formula (IV) are intermediates for the compounds represented by the general formula (I) of the present invention. These compounds are used for the production of the compounds of the present invention in accordance with the above-mentioned second process for the production.

Examples of $R_3$ being the protective group for the amino group in the compounds represented by said general formula (VI) include those employed usually in this field, for example, substituted or unsubstituted lower alkanoyl groups, such as formyl, acetyl, chloroacetyl, dichloroacetyl, propionyl, phenylacetyl, 2-thienylacetyl, 2-furylacetyl, phenoxyacetyl and the like; substituted or unsubstituted lower alkoxycarbonyl groups such as benzyloxycarbonyl, t-butoxycarbonyl, p-nitrobenzyloxycarbonyl and the like; substituted lower alkyl groups such as trityl, p-methoxybenzyl, diphenylmethyl and the like; and substituted silyl groups such as trimethylsilyl, t-butyldimethylsilyl and the like.

Examples of $R_5$ being the protective group for the carboxyl group include those employed usually in this field, for example, substituted or unsubstituted lower alkyl groups such as methyl, ethyl, propyl, t-butyl, 2,2,2-trichloroethyl, valeryloxymethyl, pivaloyloxymethyl, p-nitrobenzyl, p-methoxybenzyl, diphenylmethyl and the like; and substituted silyl groups such as trimethylsilyl, t-butyldimethylsilyl and the like.

Examples of the anion in A include halogen ions such as chloro ion, bromo ion, iodo ion and the like; and inorganic acid ions such as sulfuric acid ion, nitric acid ion and the like.

An example of salts of the compounds represented by the general formula (VI) includes inorganic acid salts such as hydrochloride, hydrobromide, hydroiodide, sulfate, carbonate, bicarbonate and the like; organic carboxylates such as, acetate, maleate, lactate, tartrate, trifluoroacetate and the like; organic sulfonates such as methanesulfonate, benzenesulfonate, toluenesulfonate and the like; and amino acid salts such as aspartate, glutamate and the like.

The compounds represented by the general formula (VI) can be produced in accordance with the following process.

A compound represented by the general formula:

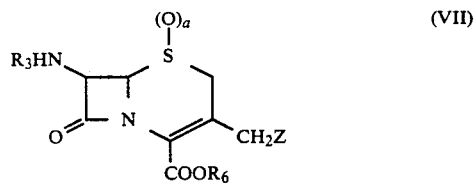

wherein a and $R_3$ have the same meanings as defined above, $R_6$ denotes hydrogen atom or a protective group for the carboxyl group, and Z is a halogen atom or a lower alkanoyloxy group, or a salt thereof is reacted with a compound represented by the general formula:

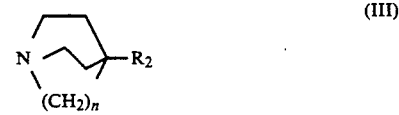

wherein n and $R_2$ have the same meanings as defined above, or with a salt thereof, followed by, if necessary, removal of the protective group and/or reduction of the sulfoxide to obtain the compounds having the aforesaid general formula (VI) or the salts thereof.

In the case wherein Z in the general formula (VII) represents a halogen atom, the above reaction may be carried out in an inert solvent such as acetone, tetrahydrofuran, N,N-dimethylformamide, methylene chloride, chloroform, acetonitrile, and the like at a reaction temperature of −10° C. to 50° C.

In the case wherein Z in the general formula (VII) represents a lower alkanoyloxy group, the above reaction may be carried out in an inert solvent such as chloroform, methylene chloride, tetrahydrofuran, N, N-dimethylformamide, dioxane, acetone, and the like in the presence of iodotrimethylsilane at a reaction temperature of −20° C. to 60° C.

The removal of protective groups may be achieved in accordance with a conventional procedure such as hydrolysis, reduction and the like, depending upon the type of the protective group used. Furthermore, the reduction of sulfoxide may be carried out by using a conventional reduction reagent such as, for example, phosphorus trichloride, and the like.

An example of Z being the halogen atom in the compound represented by the general formula (VII) includes chlorine, bromine, or iodine atom.

An example of Z being the lower alkanoyloxy group includes acetyloxy, propionyloxy, and the like.

An example of $R_6$ being the protective group for carboxyl group includes those enumerated in the description for $R_5$. Furthermore, any salt which does not inhibit said reaction may be used as the salts of the compounds represented by the general formulae (VII) and (III), and these salts may be suitably selected from the group consisting of, for example, alkali metal salts such as sodium, potassium and the like salts; alkaline earth metal salts such as calcium, magnesium and the like salts; ammonium salts; inorganic acid salts such as hydrochloride, sulfate, carbonate, bicarbonate, hydrobromide, hydroiodide, and the like; organic carboxylates such as acetate, maleate, lactate, tartrate, trifluoroacetate and the like; organic sulfonates such as methanesulfonate, benzenesulfonate, toluenesulfonate and the like; amine salts such as trimethylamine, triethylamine, pyridine, procaine, picoline, dicyclohexylamine, N, N'-dibenzylethylenediamine, N-methylglucamine, diethanolamine, triethanolamine, tris(hydroxymethylamino)methane and the like salts; and amino acid salts such as alginate, aspartate, glutamate and lysine, serine or the like salt.

The compounds of this invention showed strong antibacterial activities against both gram-positive and gram-negative bacteria. In addition, in the case of the following compounds, all of their acute toxicity levels [$LD_{50}$ (mouse, intravenous injection)] were found to be more than 3 g/kg.

7β-[(Z)-2-(2-Aminothiazol-4-yl)-2-methoxyiminoacetamido]-3-(4-hydroxy-1,4-methylene-1-piperidinio)methyl-3-cephem-4-carboxylate;

7β-[(Z)-2-(5-Amino-1,2,4-thiadiazol-3-yl)-2-methoxyiminoacetamido]-3-(4-hydroxy-1,4-methylene-1-piperidinio)methyl-3-cephem-4-carboxylate;

7β-[(Z)-2-(2-Aminothiazol-4-yl)-2-methoxyiminoacetamido]-3-(4-hydroxy-1-quinuclidinio)-methyl-3-cephem-4-carboxylate;

7β-[(Z)-2-(5-Amino-1,2,4-thiadiazol-3-yl)-2-methoxyiminoacetamido]-3-(4-hydroxy-1-quinuclidinio)-methyl-3-cephem-4-carboxylate;

7β-[(Z)-2-(2-Aminothiazol-4-yl)-2-methoxyiminoacetamido]-3-(4-carbamoyl-1-quinuclidinio)-methyl-3-cephem-4-carboxylate; and 7β-[(Z)-2-(5-Amino-1,2,4-thiadiazol-3-yl)-2-methoxyiminoacetamido]-3-(4-carbamoyl-1-quinuclidinio)-methyl-3-cephem-4-carboxylate;

When using the compounds of this invention as antibacterial agents, their dosages are 2 to 300 mg/kg/day or preferably 10 to 100 mg/kg/day.

The antibacterial composition may be administered orally in the form of powder, granules, capsules, tablets and the like, or parenterally in the form of parenteral solutions, suppositories and the like. These compositions may be prepared in a usual manner, using an effective amount of the compound of this invention and pharmaceutically-acceptable excipients.

By the way, the following nomenclature is used in the present invention.

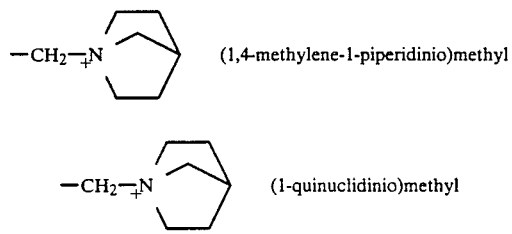

The present invention will be described in further detail by the following Experiments and Examples.

EXPERIMENT 1

Production of 4-hydroxy-1,4-methylenepiperidine

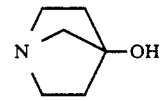

(1) 1-Benzyl-4-ethoxycarbonyl-4-hydroxypiperidine

Conc. sulfuric acid (12 ml) was added to an ethanol solution (50 ml) of 1-benzyl-4-cyano-4-hydroxypiperidine hydrochloride (10 g) and the resulting mixture was heated at 130° C. for 24 hours in a sealed tube. After concentration of the reaction mixture, ice water was added to the concentrate. The resulting mixture was added with an aqueous solution of sodium hydrogencarbonate. After adjusting the thus-obtained solution of pH 7.0, it was extracted with diethyl ether. The extract was washed with brine and then added with anhydrous sodium sulfate to dry the same. The solvent was distilled off to obtain the intended product (9.7 g).

(2) 1-Benzyl-4-hydroxymethyl-4-hydroxypiperidine

To a diethyl ether suspension (0.5 l) of lithium aluminum hydride (19.4 g), a diethyl ether solution (0.5 l) of the compound (44.6 g) obtained in the above procedure (1) was added dropwise under ice-cooling. After completion of the dropwise addition, the resulting mixture was stirred for 1.5 hrs. After addition of ethyl acetate (100 ml) and saturated aqueous sodium sulfate solution (100 ml) to the reaction mixture, the resulting mixture was filtered through Celite (trade mark). The residue was washed with tetrahydrofuran. The filtrate and washing were combined together, followed by their concentration under reduced pressure. The residue was then purified by alumina column chromatography (eluent: chloroform, 5% methanol-chloroform, and 20% methanol-chloroform) to obtain the desired product (31.5 g).

(3) 1-Benzyl-4-hydroxy-1,4-methylenepiperidine p-toluenesulfonate

To a pyridine solution (120 ml) of the compound (11.3 g) obtained in the above procedure (2), p-toluenesulfonyl chloride (10.7 g) was added at −30° C. The resulting mixture was heated to 4° C., at which it was stirred for 15 hours. The reaction mixture was concentrated under reduced pressure and the thus-obtained residue was dissolved in a small amount of ice water. After adding 2N aqueous potassium hydroxide solution (82 ml) to the above-prepared solution, the resulting solution was extracted with benzene. Anhydrous potassium carbonate was added to the extract to dry the same. After refluxing the solution for 9 hours, it was cooled to room temperature. The resulting precipitate was collected by filtration and then washed with absolute benzene to obtain the desired product (16.5 g).

(4) 4-Hydroxy-1,4-methylenepiperidine

Added to a methanol solution (300 ml) of the compound (16.5 g) obtained in the above procedure (3) was 10% palladium-carbon (50% water content; 3.3 g), followed by stirring for 3 hours in a hydrogen atmosphere. The reaction mixture was filtered and the filtrate was concentrated under reduced pressure. Saturated aqueous potassium carbonate solution was added to the residue, followed by extraction with chloroform. After adding anhydrous potassium carbonate to the extract to dry the same, the thus-dried extract was concentrated under reduced pressure to obtain the desired product (4.0 g).

Melting point: 124.0°–124.5° C.
Mass spectrum (M+): 113.
NMR spectrum (CDCl$_3$: δ): 1.70(4H,m), 2.41(2H,s), 2.75(2H,m), 3.16(2H,m).

EXAMPLE 1

7β-[(Z)-2-(2-Aminothiazol-4-yl)-2-methoxyiminoacetamido]-3-(4-hydroxy-1,4-methylene-1-piperidinio)methyl-3-cephem-4-carboxylate

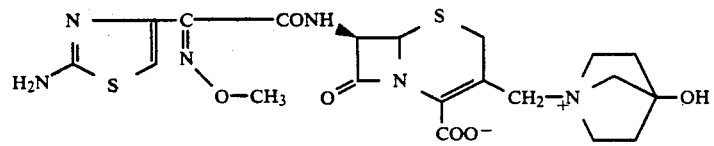

7β-[(Z)-2-(2-Aminothiazol-4-yl)-2-methoxyiminoacetamido]-3-acetoxymethyl-3-cephem-4-carboxylic acid (240 mg) was suspended in methylene chloride (4 ml), followed by an addition of N-methyl-N-(trimethylsilyl) trifluoroacetamide (330 μl). The resulting mixture was stirred at room temperature for 30 minutes. After ice-cooling, iodotrimethylsilane (200 μl) was added to the solution, and the resulting mixture was stirred at room temperature for 15 minutes. The reaction mixture was concentrated under reduced pressure to obtain the silylated derivative of 7β-[(Z)-2-(2-aminothiazol-4-yl)-2-methoxyiminoacetamido]-3-iodomethyl-3-cephem-4-carboxylic acid.

The silylated derivative was dissolved in acetonitrile (3 ml), followed by an addition of tetrahydrofuran (60 μl). The thus-obtained solution was added with 4-hydroxy-1,4-methylenepiperidine (72 mg) and the resulting mixture was stirred at room temperature for 2 hours. Methanol (0.3 ml) was then added to the reaction mixture and the resulting mixture was stirred for 15 minutes. The resulting precipitate was collected by filtration and then washed with acetonitrile. The precipitate was dissolved in 30% ethanol. Subsequent to its concentration under reduced pressure, the residue was dissolved in a 7:1 mixed solvent of acetone and water. The resulting solution was purified by silica gel column chromatography (eluent: 9:1 and 7:1 mixed solvent of acetone and water) to obtain the desired product (39 mg).

EXAMPLE 2

7β-[(Z)-2-(5-Amino-1,2,4-thiadiazol-3-yl)-2-methoxyiminoacetamido]-3-(4-hydroxy-1,4-methylene-1-piperidinio)methyl-3-cephem-4-carboxylate

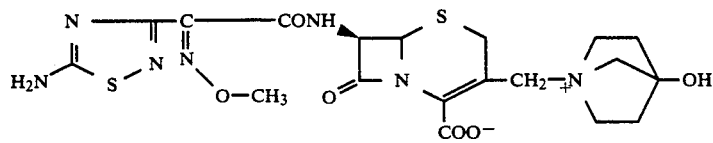

7β-[(Z)-2-(5-Amino-1,2,4-thiadiazol-3-yl)-2-methoxyiminoacetamido]-3-acetoxymethyl-3-cephem-4-carboxylic acid (319 mg) was suspended in methylene chloride (4 ml), followed by an addition of N-methyl-N-(trimethylsilyl)trifluoroacetamide (877 μl). The resulting mixture was stirred at room temperature for 1 hour. After ice-cooling, iodotrimethylsilane (268 μl) was added and the resulting mixture was stirred for 15 minutes. The reaction mixture was concentrated under reduced pressure to obtain the silylated derivative of 7β-[(Z)-2-(5-amino-1,2,4-thiadiazol-3-yl)-2-methoxyiminoacetamido]-3-iodomethyl-3-cephem-4-carboxylic acid.

The silylated derivative was dissolved in acetonitrile (3.6 ml). The thus-obtained solution was added with 4-hydroxy-1,4-methylenepiperizine (71 mg) and the resulting mixture was stirred for 2 hours with ice-cooling. Methanol (0.3 ml) was then added to the reaction mixture and the resulting mixture was stirred for 15 minutes. The resulting precipitate was collected by filtration and then washed with acetonitrile. The precipitate was dissolved in 30% ethanol. Subsequent to its concentration under reduced pressure, the residue was dissolved in a 7:1 mixed solvent of acetone and water. The resulting solution was purified by silica gel column chromatography (eluent: 7:1 and 5:1 mixed solvent of acetone and water) to obtain the desired product (29 mg).

EXAMPLE 3

7β-[(Z)-2-(2-Aminothiazol-4-yl)-2-methoxyiminoacetamido]-3-(4-hydroxy-1-quinuclidinio)methyl-3-cephem-4-carboxylate

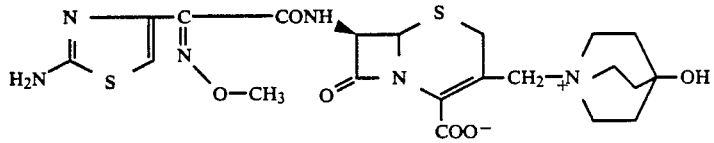

7β-[(Z)-2-(2-Aminothiazol-4-yl)-2-methoxyiminoacetamido]-3-acetoxymethyl-3-cephem-4-carboxylic acid (977 mg) was suspended in methylene chloride (16 ml), followed by an addition of N-methyl-N-(trimethylsilyl) trifluoroacetamide (1350 μl). The resulting mixture was stirred at room temperature for 1 hour. After ice-cooling, iodotrimethylsilane (810 μl) was added and the resulting mixture was stirred for 15 minutes. The reaction mixture was concentrated under reduced pressure to obtain the silylated derivative of 7β-[(Z)-2-(2-aminothiazol-4-yl)-2-methoxyiminoacetamido]-3-iodomethyl-3-cephem-4-carboxylic acid.

The silylated derivative was dissolved in acetonitrile (12 ml), followed by an addition of tetrahydrofuran (240 μl). The thus-obtained solution was added with 4-hydroxyquinuclidine (300 mg) and the resulting mixture was stirred at room temperature for 1.5 hours. Methanol (1.2 ml) was then added to the reaction mixture and the resulting mixture was stirred for 15 minutes. The resulting precipitate was collected by filtration and then washed with acetonitrile. The precipitate was dissolved in 30% ethanol. Subsequent to its concentration under reduced pressure, the residue was dissolved in a 7:1 mixed solvent of acetone and water. The resulting solution was purified by silica gel column chromatography (eluent: 7:1 mixed solvent of acetone and water) to obtain the desired product (38 mg).

EXAMPLE 4

7β-[(Z)-2-(5-Amino-1,2,4-thiadiazol-3-yl)-2-methoxyiminoacetamido]-3-(4-hydroxy-1-quinuclidinio)methyl-3-cephem-4-carboxylate

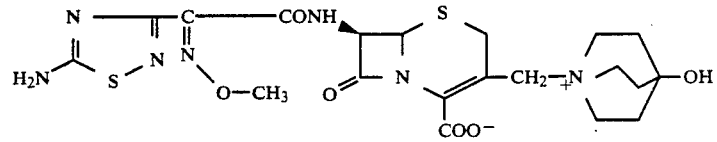

7β-[(Z)-2-(5-Amino-1,2,4-thiadiazol-3-yl)-2-methoxyiminoacetamido]-3-acetoxymethyl-3-cephem-4-carboxylic acid (486 mg) was suspended in methylene chloride (9 ml), followed by an addition of N-methyl-N-(trimethylsilyl)trifluoroacetamide (980 μl). The resulting mixture was stirred at room temperature for 1 hour. After ice-cooling, iodotrimethylsilane (410 μl) was added and the resulting mixture was stirred for 15 minutes. The reaction mixture was concentrated under reduced pressure to obtain the silylated derivative of 7β-[(Z)-2-(5-amino-1,2,4-thiadiazol-3-yl)-2-methoxyiminoacetamido]-3-iodomethyl-3-cephem-4-carboxylic acid.

The silylated derivative was dissolved in acetonitrile (6 ml), followed by an addition of tetrahydrofuran (130 μl). The resulting solution was added with 4-hydroxyquinuclidine (150 mg) and the resulting mixture was stirred at room temperature for 1 hour. Methanol (0.6 ml) was then added to the reaction mixture and the resulting mixture was stirred for 15 minutes. The resulting precipitate was collected by filtration and then washed with acetonitrile. The precipitate was dissolved in 30% ethanol. Subsequent to its concentration under reduced pressure, the residue was purified by silica gel column chromatography (eluent: 9:1 mixed solvent of acetone and water) to obtain the desired product (13 mg).

EXAMPLE 5

7β-[(Z)-2-(2-Aminothiazol-4-yl)-2-methoxyiminoacetamido]-3-(4-carbamoyl-1-quinuclidinio)-methyl-3-cephem-4-carboxylate

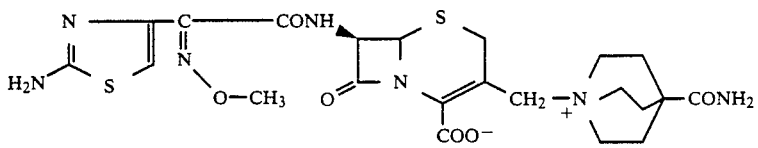

7β-[(Z)-2-(2-Aminothiazol-4-yl)-2-methoxyiminoacetamido]-3-acetoxymethyl-3-cephem-4-carboxylic acid (240 mg) was suspended in methylene chloride (4 ml), followed by an addition of N-methyl-N-(trimethylsilyl) trifluoroacetamide (330 μl). The resulting mixture was stirred at room temperature for 30 minutes. After ice-cooling, iodotrimethylsilane (200 μl) was added and the resulting mixture was stirred for 15 minutes. The reaction mixture was then concentrated under reduced pressure to obtain the silylated derivative of 7β-[(Z)-2-(2-aminothiazol-4-yl)-2-methoxyiminoacetamido]-3-iodomethyl-3-cephem-4-carboxylic acid.

The silylated derivative was dissolved in acetonitrile (3 ml), followed by an addition of tetrahydrofuran (60 μl). The resulting solution was added with 4-carbamoylquinuclidine (98 mg) and the resulting mixture was stirred at room temperature for 2 hours. Methanol (0.3 ml) was then added to the reaction mixture and the resulting mixture was stirred at room temperature for 15 minutes. The resulting precipitate was collected by filtration and then washed with acetonitrile. The precipitate was dissolved in 30% ethanol. Subsequent to its concentration under reduced pressure, the residue was dissolved in a 7:1 mixed solvent of acetone and water. The thus-obtained solution was purified by silica gel column chromatography (eluent: 7:1 mixed solvent of acetone and water) to obtain the desired product (53 mg).

EXAMPLE 6

7β-[(Z)-2-(5-Amino-1,2,4-thiadiazol-3-yl)-2-methox-yiminoacetamido]-3-(4-carbamoyl-1-quinuclidinio)-methyl-3-cephem-4-carboxylate

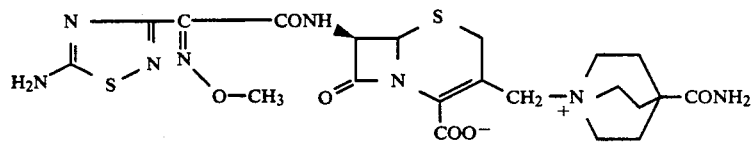

7β-[(Z)-2-(5-Amino-1,2,4-thiadiazol-3-yl)-2-methox-yiminoacetamido]-3-acetoxymethyl-3-cephem-4-carboxylic acid (790 mg) was suspended in methylene chloride (10 ml), followed by an addition of N-methyl-N-(trimethylsilyl)trifluoroacetamide (2.1 ml). The resulting mixture was stirred at room temperature for 1 hour. After ice-cooling, iodotrimethylsilane (660 μl) was added and the resulting mixture was stirred for 15 minutes. The reaction mixture was concentrated under reduced pressure to obtain the silylated derivative of 7β-[(Z)-2-(5-amino-1,2,4-thiadiazol-3-yl)-2-methox-yiminoacetamido]-3-iodomethyl-3-cephem-4-carboxylic acid.

The silylated derivative was dissolved in acetonitrile (9 ml), followed by an addition of 4-carbamoylquinuclidine (240 mg). The resulting mixture was stirred for 1 hour with ice-cooling. Methanol (0.6 ml) was then added to the reaction mixture and the resulting mixture was stirred for 15 minutes. The resulting precipitate was collected by filtration and then washed with acetonitrile. The precipitate was dissolved in 30% ethanol. Subsequent to its concentration under reduced pressure, the residue was dissolved in 7:1 mixed solvent of acetone and water. The solution was purified by silica gel column chromatography (eluent: 7:1 and 5:1 mixed solvents of acetone and water) to obtain the desired product (326 mg).

EXAMPLE 7

7β-[(Z)-2-(5-Amino-1,2,4-thiadiazol-3-yl)-2-carboxyme-thoxyiminoacetamido]-3-(4-hydroxy-1,4-methylene-1-piperidinio)methyl-3-cephem-4-carboxylate

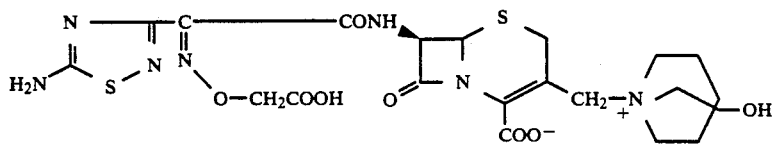

Similar to Examples 1-6, the silylated derivative of 7β-[(Z)-2-(5-amino-1,2,4-thiadiazol-3-yl)-2-carboxyme-thoxyiminoacetamido]-3-iodomethyl-3-cephem-4-carboxylic acid was obtained from 7β-[(Z)-2-(5-amino-1,2,4-thiadiazol-3-yl)-2-carboxymethox-yiminoacetamido]-3-acetoxymethyl-3-cephem-4-carboxylic acid (500 mg), N-methyl-N-(trimethylsilyl)tri-fluoroacetamide (1.23 ml) and iodotrimethylsilane (780 μl). The silylated derivative was reacted with 4-hydroxy-1,4-methylenepiperidine (90 mg) to obtain the desired product (113 mg).

EXAMPLE 8

7β-[(Z)-2-(2-Aminothiazol-4-yl)-2-methox-yiminoacetamido]-3-(4-hydroxymethyl-1-quinuclidini-o)methyl-3-cephem-4-carboxylate

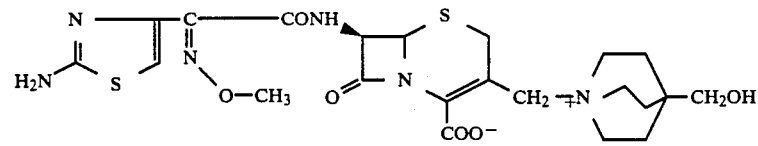

Similar to Examples 1-6, the silylated derivative of 7β-[(Z)-2-(2-aminothiazol-4-yl)-2-methox-yiminoacetamido]-3-iodomethyl-3-cephem-4-carboxylic acid was obtained from 7β-[(Z)-2-(2-aminothiazol-4-yl)-2-methoxyiminoacetamido]-3-acetoxymethyl-3-cephem-4-carboxylic acid (240 mg), N-methyl-N-(trimethylsilyl)trifluoroacetamide (330 μl) and iodo-trimethylsilane (300 μl). The silylated derivative was reacted with 4-hydroxymethylquinuclidine (89 mg) to obtain the desired product (6 mg).

EXAMPLE 9

7β-[(Z)-2-(2-Aminothiazol-4-yl)-2-propargyloxyiminoacetamido]-3-(4-carbamoyl-1-quinuclidinio)-methyl-3-cephem-4-carboxylate

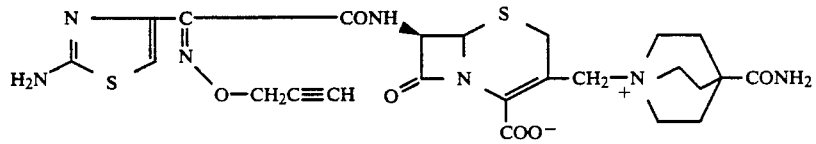

Similar to Examples 1–6, the silylated derivative of 7β-[(Z)-2-(2-aminothiazol-4-yl)-2-propargyloxyiminoacetamido]-3-iodomethyl-3-cephem-4-carboxylic acid was obtained from 7β-[(Z)-2-(2-aminothiazol-4-yl)-2-propargyloxyiminoacetamido]-3-acetoxymethyl-3-cephem-4-carboxylic acid (290 mg), N-methyl-N-(trimethylsilyl)trifluoroacetamide (380 μl) and iodotrimethylsilane (230 μl). The silylated derivative was reacted with 4-carbamoylquinuclidine (112 mg) to obtain the desired product (10 mg).

EXAMPLE 10

7β-[(Z)-2-(2-Aminothiazol-4-yl)-2-carbamoylmethoxyiminoacetamido]-3-(4-carbamoyl-1-quinuclidinio)-methyl-3-cephem-4-carboxylate

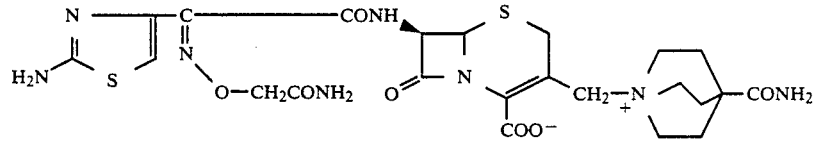

Similar to Examples 1–6, the silylated derivative of 7β-[(Z)-2-(2-aminothiazol-4-yl)-2-carbamoylmethoxyiminoacetamido]-3-iodomethyl-3-cephem-4-carboxylic acid was obtained from 7β-[(Z)-2-(2-aminothiazol-4-yl)-2-carbamoylmethoxyiminoacetamido]-3-acetoxymethyl-3-cephem-4-carboxylic acid (110 mg), N-methyl-N-(trimethylsilyl)trifluoroacetamide (140 μl) and iodotrimethylsilane (180 μl). The silylated derivative was reacted with 4-carbamoylquinuclidine (41 mg) to obtain the desired product (5 mg).

EXAMPLE 11

7β-[(Z)-2-(5-Amino-1,2,4-thiadiazol-3-yl)-2-ethoxyiminoacetamido]-3-(4-carbamoyl-1-quinuclidino)-methyl-3-cephem-4-carboxylate

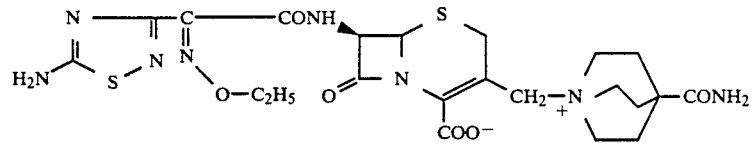

Similar to Examples 1–6, the silylated derivative of 7β-[(Z)-2-(5-amino-1,2,4-thiadiazol-3-yl)-2-ethoxyiminoacetamido]-3iodomethyl-3-cephem-4-carboxylic acid was obtained from 7β-[(Z)-2-(5-amino-1,2,4-thiadiazol-3-yl)-2-ethoxyiminoacetamido]-3-acetoxymethyl-3-cephem-4-carboxylic acid (300 mg), N-methyl-N-(trimethylsilyl)trifluoroacetamide (600 μl) and iodotrimethylsilane (500 μl). The silylated derivative was reacted with 4-carbamoylquinuclidine (118 mg) to obtain the desired product (62 mg).

EXAMPLE 12

7β-[(Z)-2-(5-Amino-1,2,4-thiadiazol-3-yl)-2-(1-carboxy-1-methylethoxy)iminoacetamido]-3-(4-carbamoyl-1-quinuclidinio)methyl-3-cephem-4-carboxylate

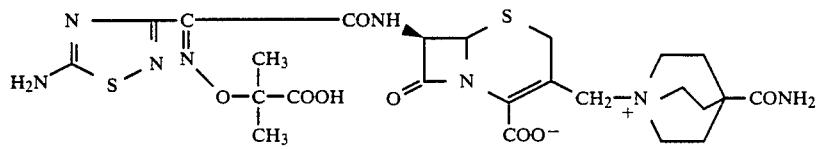

Similar to Examples 1–6, the silylated derivative of 7β-[(Z)-2-(5-amino-1,2,4-thiadiazol-3-yl)-2-(1-carboxy-1-methylethoxy)iminoacetamido]-3-iodomethyl-3-cephem-4-carboxylic acid was obtained from 7β-[(Z)-2-(5-amino-1,2,4-thiadiazol-3-yl)-2-(1-carboxy-1-methoxyethoxy)iminoacetamido]-3-acetoxymethyl-3-cephem-4-carboxylic acid (530 mg), N-methyl-N-(trimethylsilyl)-trifluoroacetamide (820 μl) and iodotrimethylsilane (390 μl). The silylated derivative was reacted with 4-carbamoylquinuclidine (186 mg) to obtain the desired product (100 mg).

EXAMPLE 13

7β-[(Z)-2-(5-Amino-1,2,4-thiadiazol-3-yl)-2-carboxymethoxyiminoacetamido]-3-(4-carbamoyl-1-quinuclidinio)methyl-3-cephem-4-carboxylate

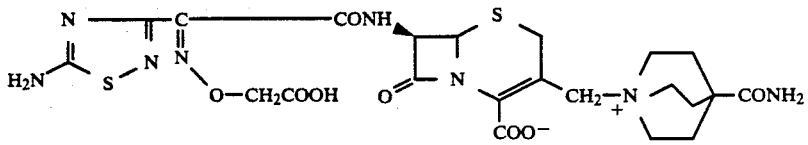

Similar to Examples 1-6, the silylated derivative of 7β-[(Z)-2-(5-amino-1,2,4-thiadiazol-3-yl)-2-carboxymethoxyiminoacetamido]-3-iodomethyl-3-cephem-4-carboxylic acid was obtained from 7β-[(Z)-2-(5-amino-1,2,4-thiadiazol-3-yl)-2-carboxymethoxyiminoacetamido]-3-acetoxymethyl-3-cephem-4-carboxylic acid (500 mg), N-methyl-N-(trimethylsilyl)trifluoroacetamide (1.23 μl) and iodotrimethylsilane (780 μl). The silylated derivative was reacted with 4-carbamoylquinuclidine (142 mg) to obtain the desired product (36 mg).

EXAMPLE 14

7β-[(Z)-2-(5-Amino-1,2,4-thiadiazol-3-yl)-2-methoxyiminoacetamido]-3-[4-hydroxymethyl-1-quinuclidinio]methyl-3-cephem-4-carboxylate

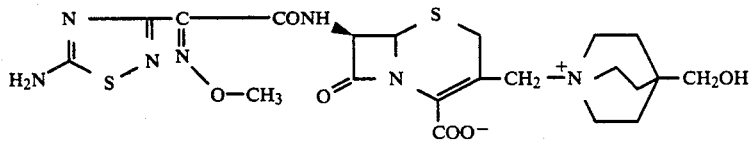

Similar to Examples 1-6, the silylated derivative of 7β-[(Z)-2-(5-amino-1,2,4-thiadiazol-3-yl)-2-methoxyiminoacetamido]-3-iodomethyl-3-cephem-4-carboxylic acid was obtained from 7β-[(Z)-2-(5-amino-1,2,4-thiadiazol-3-yl)-2-methoxyiminoacetamido]-3-acetoxymethyl-3-cephem-4-carboxylic acid (460 mg), N-methyl-N-(trimethylsilyl)trifluoroacetamide (640 μl), and iodotrimethylsilane (390 μl). The silylated derivative was reacted with 4-hydroxylmethylquinuclidine (142 mg) to obtain the desired product (8 mg).

EXAMPLE 15

7β-[(Z)-2-(5-Amino-1,2,4-thiadiazol-3-yl)-2-methoxyiminoacetamido]-3-(4-methyl-1-quinuclidinio)methyl-3-cephem-4-carboxylate

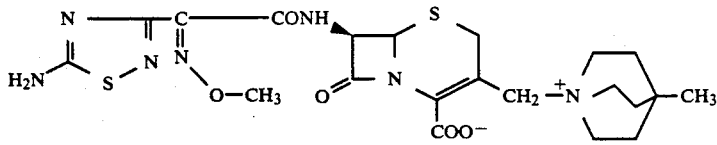

p-Methoxybenzyl 7β-[(Z)-2-(5-amino-1,2,4-thiadiazol-3-yl)-2-methoxyiminoacetamido]-3-iodomethyl-3-cephem-4-carboxylate (700 mg) was dissolved in a mixed solution of ethyl acetate (50 ml) and methanol (1 ml). After the whole was ice-cooled, a solution of ethyl acetate (2.8 ml) of 4-methyl-quinuclidine (114 mg) was added thereto, and the mixture was stirred for 15 minutes. The resulting precipitate was recovered by filtration, followed by washing with ethyl acetate to obtain p-methoxybenzyl 7β-[(Z)-2-(5-amino1,2,4-thiadiazol-3-yl)-2-methoxyiminoacetamido]-3-(4-methyl-1-quinuclidinio)methyl-3-cephem-4-carboxylate iodide (770 mg).

This compound (770 mg) was suspended in methylene chloride (8 ml). After ice-cooling, anisole (510 μl) and trifluoroacetic acid (730 μl) were added thereto. The mixture was stirred for 4 hours, followed by stirring for an additional 2.5 hours at room temperature. The resulting reaction solution was dropped in diisopropyl ether (30 ml), and the resulting precipitate was collected by filtration. The precipitate dissolved in water (5 ml). The solution was adjusted to pH of 5.0 by the addition of sodium hydrogen-carbonate. The mixture was subjected to a reversed phase silica gel column chromatography (eluent: water→5% methanol solution) for purification, to obtain the desired product (27 mg).

EXAMPLE 16

7β-[(Z)-2-(5-Amino-1,2,4-thiadiazol-3-yl)-2-cyclopropylmethoxyiminoacetamido]-3-(4-carbamoyl-1-quinuclidinio)methyl-3-cephem-4-carboxylate

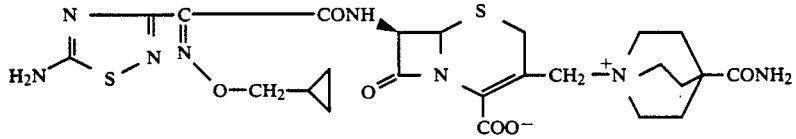

p-Methoxybenzyl 7β-[(Z)-2-(5-t-butoxycarboxamido-1,2,4-thiadiazol-3-yl)-2-cyclopropylmethoxyiminoacetamido]-3-iodomethyl-3-cephem-4-carboxylate (450 mg) was dissolved in ethyl acetate (30 ml).

After ice-cooling, there was added a mixted solution of methanol (1 ml) and ethyl acetate (5 ml) of 4-carbamoylquinuclidine (80 mg), and the whole was stirred for 30 minutes. The formed precipitate was collected by filtration, followed by washing with ethyl acetate to obtain p-methoxybenzyl 7β-[(Z)-2-(5-t-butoxycarboxamido-1,2,4-thiadiazol-3-yl)-2-cyclopropylmethoxyiminoacetamido]-3-(4-carbamoyl-1-quinuclidinio)-methyl-3-cephem-4-carboxylate iodide (290 mg).

This compound (290 mg) was dissolved in formic acid (6 ml), and the resulting solution was stirred for a day at room temperature. To the reaction solution were added acetone (10 ml), diisopropyl ether (30 ml) and n-hexane (50 ml). The formed precipitate was filtered off, and the filtrate was concentrated under a reduced pressure. The residue was dissolved in a water-methanol solution (10 ml), and the solution was adjusted to pH of 5.5 by the addition of sodium hydrogencarbonate. The resulting solution was concentrated, followed by purifying through reversed phase silica gel column chromatography (eluent: water→5% methanol solution) to obtain the desired product (19 mg).

EXAMPLE 17

7β-[(Z)-2-(5-amino-1,2,4-thiadiazol-3-yl)-2-cyclopropylmethoxyiminoacetamido]-3-(4-hydroxymethyl-1-quinuclidinio)methyl-3-cephem-4-carboxylate

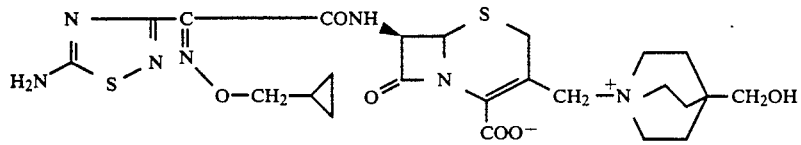

Similar to Example 16, p-methoxybenzyl 7β-[(Z)-2-(5-t-butoxycarboxamido-1,2,4-thiadiazol-3-yl)-2-cyclopropylmethoxyiminoacetamido]-3-iodomethyl-3-cephem-4-carboxylate (450 mg) was reacted with 4-hydroxymethylquinuclidine (73 mg) to obtain p-methoxybenzyl 7β-[(Z)-2-(5-t-butoxycarboxamido-1,2,4-thiadiazol-3-yl)-2-cyclopropylmethoxyiminoacetamido]-3-(4-hydroxymethyl-1-quinuclidinio)methyl-3-cephem-4-carboxylate (310 mg), followed by removing a protective group by means of formic acid to obtain the desired product (23 mg).

TABLE 1

Physical Date

| Example No. | IR absorption spectrum (cm$^{-1}$, Nujol) | NMR spectrum (δ, D$_2$O) |
|---|---|---|
| 1 | 1765 | 2.30(4H, m), 3.20–4.40(m), 4.08(3H, s), 5.43(1H, d, J=6Hz), 5.94(1H, d, J=6Hz), 7.09(1H, s). |
| 2 | 1775 | 2.32(4H, m), 3.30–4.00(m), 4.18(3H, s), 5.43(1H, d, J=6Hz), 5.98(1H, d, J=6Hz) |
| 3 | 1765 | 2.20(6H, m), 3.40–4.00(m), 4.10(3H, s), 5.44(1H, d, J=6Hz), 5.96(1H, d, J=6Hz), 7.10(1H, s). |
| 4 | 1765 | 2.20(6H, m), 3.30–4.00(m), 4.18(3H, s), 5.43(1H, d, J=6Hz), 5.97(1H, d, J=6Hz). |
| 5 | 1770 | 2.30(6H, m), 3.30–4.00(m), 4.10(3H, s), 5.45(1H, d, J=6Hz), 5.97(1H, d, J=6Hz), 7.12(1H, s). |
| 6 | 1775 | 2.30(6H, m), 3.15–4.00(m), 4.16(3H, s), 5.43(1H, d, J=6Hz), 5.97(1H, d, J=6Hz). |
| 7 | 1760 | 2.30(4H, m), 3.00–4.30(m), 4.77(2H, s), 5.42(1H, d, J=6Hz), 5.99(1H, d, J=6Hz). |
| 8 | 1770 | 1.96(6H, m), 3.20–4.00(m), 4.12(3H, s), 5.47(1H, d, J=6Hz), 5.97(1H, d, J=6Hz), 7.15(1H, s). |
| 9 | 1765 | 2.24(6H, m), 3.20–4.20(m), 5.47(1H, d, J=6Hz), 5.99(1H, d, J=6Hz), 7.19(1H, s). |
| 10 | 1770 | 2.30(6H, m), 3.30–4.20(m), 5.48(1H, d, J=6Hz), 6.00(1H, d, J=6Hz), 7.22(1H, s). |
| 11 | 1770 | 1.45(3H, t, J=8Hz), 2.30(6H, m), 3.20–4.20(m), 4.46(2H, q, J=8Hz), 5.46(1H, d, J=6Hz), 6.00(1H, d, J=6Hz). |
| 12 | 1770 | 1.65(6H, s), 2.25(6H, m), 3.30–4.20(m), 5.47(1H, d, J=6Hz), 6.01(1H, d, J=6Hz). |
| 13 | 1765 | 2.30(6H, m), 3.20–4.30(m), 5.44(1H, d, J=5Hz), 6.00(1H, d, J=5Hz). |
| 14 | 1770 | 1.96(6H, m), 3.20–4.30(m), 4.19(3H, s) 5.44(1H, d, J=6Hz), 5.99(1H, d, J=6Hz). |
| 15 | 1765 | 1.14(3H, s), 1.94(6H, m), 3.30–4.20(m), 4.20(3H, s), 5.47(1H, d, J=6Hz), 6.01(1H, d, J=6Hz) |
| 16 | 1770 | 0.30–0.90(4H, m), 1.37(1H, m), 2.30(6H, m), 3.20–4.20(m), 4.25(2H, d, J=8Hz), 5.47(1H, d, J=5Hz), 6.02(1H, d, J=5Hz). |
| 17 | 1770 | 0.30–0.90(4H, m), 1.37(1H, m), 2.04(6H, m), 3.20–4.10(m) 4.25(2H, d, J=8Hz), 5.48(1H, d, J=6Hz), 6.03(1H, d, J=6Hz). |

EXPERIMENT 2

7β-Formamido-3-(4-carbamoyl-1-quinuclidinio)methyl-3-cephem-4-carboxylate

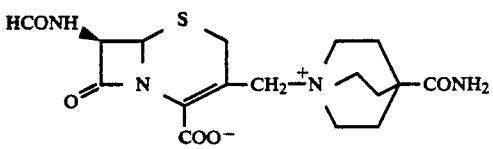

7β-Formamido-3-acetoxymethyl-3-cephem-4-carboxylic acid (1.2 g) was suspended in methylene chloride (12 ml), and then N-methyl-N-(trimethylsilyl)trifluoroacetamide (815 μl) was added thereto and stirred for 30 minutes. After cooling the mixture with ice, iodotrimethylsilane (1.25 ml) was added thereto and stirred for 5 minutes, thereafter the temperature of the mixture was returned to room temperature, and the mixture was stirred for another 15 minutes. Solvent was distilled away under reduced pressure from the resulting solution, and the residue was dissolved in acetonitrile (12 ml). 4-Carbamoylquinuclidine (616 mg) was added to the solution under ice-cooling and stirred for 1 hour. To the reaction solution was added methanol (3 ml) and further diethyl ether (300 ml), and the resulting precipitate was filtered.

The precipitate was purified by means of silica gel column chromatography [eluent: acetone-water (7:1) and (5:1)] to obtain the desired product (140 mg).

EXPERIMENT 3

7β-Tritylamino-3-(4-carbamoyl-1-quinuclidinio)methyl-3-cephem-4-carboxylate

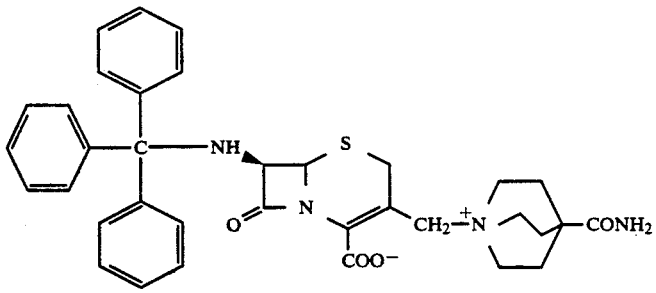

7β-Tritylamino-3-acetoxymethyl-3-cephem-4-carboxylic acid (2.4 g) was dissolved in methylene chloride (24 ml), and then N-methyl-N-(trimethylsilyl)trifluoroacetamide (960 μl) was added thereto and stirred for 30 minutes. After cooling the mixture with ice, iodotrimethylsilane (720 μl) was added thereto and stirred for 5 minutes, thereafter the temperature of the mixture was returned to room temperature, and the mixture was stirred for another 15 minutes. Solvent was distilled away under reduced pressure from the resulting solution, and the residue was dissolved in acetonitrile (12 ml). 4-Carbamoylquinuclidine (756 mg) was added to the solution under ice-cooling and stirred for 1 hour. To the reaction solution was added methanol (3.2 ml) and then diethyl ether (240 ml), and the resulting precipitate was filtered.

The precipitate was purified by means of silica gel column chromatography [eluent: acetone-water (7:1), (5:1), and (3:1)] to obtain the desired product (207 mg).

EXPERIMENT 4

7β-(2-Thienylacetamido)-3-(4-carbamoyl-1-quinuclidinio)methyl-3-cephem-4-carboxylate

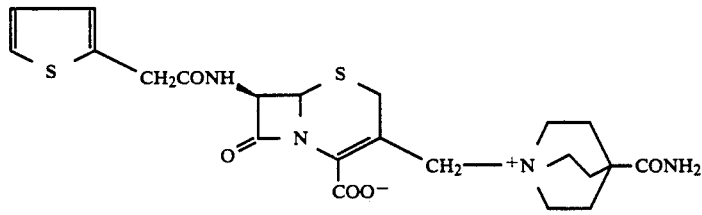

7β-(2-Thienylacetamido)-3-acetoxymethyl-3-cephem-4-carboxylic acid (6.0 g) was suspended in methylene chloride (60 ml), and then N-methyl-N-(trimethylsilyl)-trifluoroacetamide (3.08 ml) was added thereto and stirred for 30 minutes. After cooling the mixture with ice, iodotrimethylsilane (4.73 ml) was added thereto and stirred for 5 minutes, thereafter the mixture was further stirred at room temperature for another 15 minutes. The resulting solution was concentrated under reduced pressure, and the residue was dissolved in acetonitrile (60 ml). After ice-cooling the resulting solution, 4-carbamoylquinuclidine (2.3 g) was added to the solution and stirred for 1 hour. To the reaction solution was added methanol (6 ml), and then diethyl ether (600 ml) was dropped thereto. After stirring the mixture for 1 hour, the resulting precipitate was filtered.

The precipitate was purified by means of silica gel column chromatography [eluent: acetone-water (7:1) and (5:1)] to obtain the desired product (700 mg).

EXPERIMENT 5

7β-Amino-3-(4-carbamoyl-1-quinuclidinio)methyl-3-cephem-4-carboxylate hydrochloride

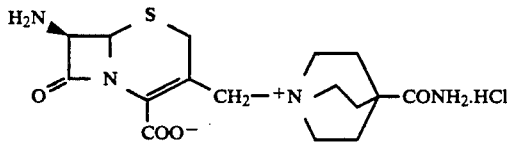

The compound (130 mg) prepared in Experiment 2 was suspended in methanol (5 ml), and concentrated hydrochloric acid (0.52 ml) was added to the suspension at room temperature and stirred for 4 hours. The reaction mixture was concentrated under reduced pressure and crystallized by means of ethyl ether-methanol, whereby the desired product (115 mg) was obtained.

EXPERIMENT 6

7β-Amino-3-(4-carbamoyl-1-quinuclidinio)methyl-3-cephem-4-carboxylate hydrochloride

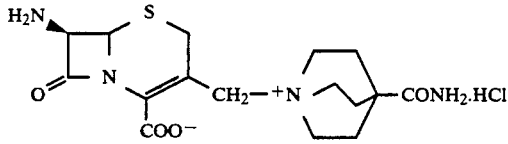

The compound (100 mg) prepared in Experiment 3 was suspended in 50% formic acid (5 ml), and stirred at room temperature for 3.5 hours. To the suspension was added water (20 ml) and insoluble matter was filtered off, and the filtrate was concentrated under reduced pressure. The residue was dissolved in 1N hydrochloric acid (1 ml), and propanol (5 ml) and diethyl ether (10 ml) was added thereto. The precipitate was filtered, washed with n-hexane, and then dried, whereby the desired product (45 mg) was obtained.

EXPERIMENT 7

7β-Amino-3-(4-carbamoyl-1-quinuclidinio)methyl-3-cephem-4-carboxylate hydrochloride

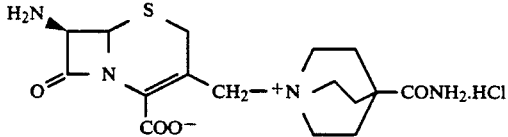

The compound (600 mg) prepared in Experiment 4 was suspended in methylene chloride (30 ml), N,N-dimethylaniline (1.24 ml) and chlorotrimethylsilane (465 μl) were added thereto, and mixture was stirred at 30° C. for 3 hours. Then, the reaction mixture was cooled to −25° C., thereafter phosphorus pentachloride (1.27 g) was added thereto, and the mixture was stirred for 1 hour. To the solution was added an ice-cooled solution of 1,3-butanediol (1.3 ml) in methylene chloride (25 ml), and the mixture was stirred at the same temperature for 10 minutes. The reaction mixture was warmed to 0° C. and stirred further for 40 minutes, and then the resulting precipitate was filtered. The precipitate was dissolved in methanol (7 ml), and the insoluble matter was filtered off. Thereafter methylene chloride (20 ml) and diethyl ether (20 ml) were added to the filtrate, so that the precipitate was filtered to obtain the desired product (30 mg).

EXPERIMENT 8 t-Butyl 7β-amino-3-(4-carbamoyl-1-quinuclidinio)methyl-3-cephem-4-carboxylate 1-oxide bromide

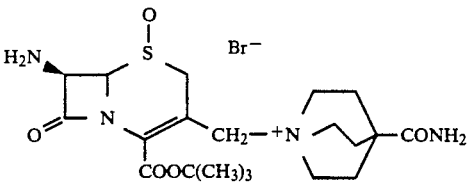

t-Butyl 7β-amino-3-bromomethyl-3-cephem-4-carboxylate 1-oxide hydrobromide (600 mg) was dissolved in N,N-dimethylformamide (6 ml), and 4-carbamoyl-quinuclidine (456 mg) was added thereto, and the mixture was stirred in argon gas stream at room temperature for 14 hours. To the reaction solution was added diethyl ether (120 ml), the resulting precipitate was filtered and washed with n-hexane, whereby the desired product (580 mg) was obtained.

EXPERIMENT 9 t-Butyl 7β-amino-3-(4-carbamoyl-1-quinuclidinio)methyl-3-cephem-4-carboxylate bromide hydrochloride

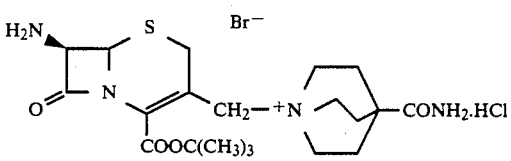

The compound (570 mg) prepared in Experiment 8 was dissolved in N,N-dimethylformamide (10 ml), phosphorus trichloride (500 μl) was added to the solution at −25° C. and stirred for 30 minutes. To the reaction solution was added diethyl ether (50 ml), so that the separated oil was taken out and washed with diethyl ether, thereafter the resulting solid was dried under reduced pressure to obtain the desired product (164 mg).

EXPERIMENT 10

7β-Amino-3-(4-carbamoyl-1-quinuclidinio)methyl-3-cephem-4-carboxylate

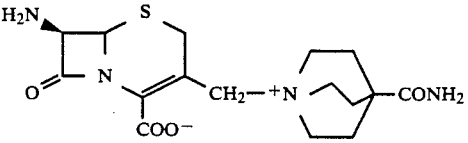

To the compound (150 mg) prepared in Experiment 9 was added formic acid (1.5 ml) and concentrated hydrochloric acid (0.15 ml) under ice-cooled condition, and the mixture was stirred for 4 hours, thereafter concentrated under reduced pressure. The residue was dissolved in ice water (5 ml) and neutralized with sodium bicarbonate. The resulting product was purified with

EXPERIMENT 11 p-Methoxybenzyl
7β-phenylacetamido-3-(4-carbamoyl-1-quinuclidinio)-methyl-3-cephem-4-carboxylate iodide

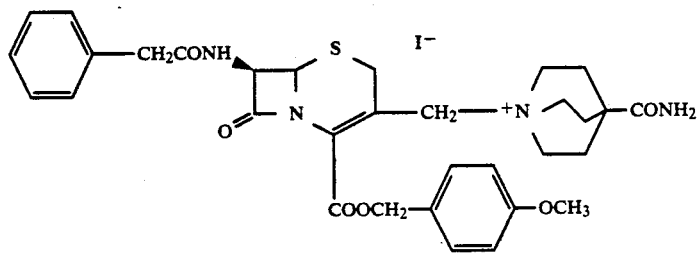

p-Methoxybenzyl 7β-phenylacetamido-3-chloromethyl-3-cephem-4-carboxylate (980 mg) was suspended in acetone (20 ml), and sodium iodide (362 mg) was added to the suspension and stirred at room temperature for 1 hour. To the resulting suspension was added 4-carbamoylquinuclidine (313 mg) under ice-cooled condition, and the mixture was stirred for 2 hours. The reaction mixture was filtered, and diethyl ether (70 ml) was added to the filtrate. The deposited solid was filtered to obtain the desired product (500 mg).

EXPERIMENT 12 p-Methoxybenzyl
7β-formamido-3-(4-carbamoyl-1-quinuclidinio)methyl-3-cephem-4-carboxylate iodide

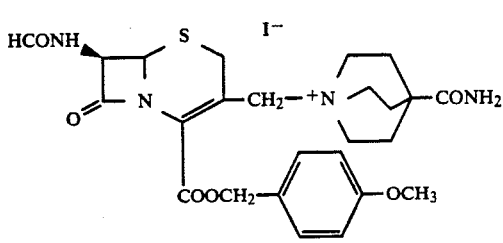

To an ethyl acetate solution (465 ml) of p-methoxybenzyl 7β-formamido-3-iodomethyl-3-cephem-4-carboxylate (9.3 g) there was added dropwise over 1 hour under stirring while ice-cooling a mixed solution (176 ml) of methanol and ethyl acetate (1:4 v/v) containing 4-carbamoyl quinuclidine (2.94 g). After stirring for 30 minutes, the resulting precipitate was collected by filtration, followed by washing with ethyl acetate and then diisopropyl ether to obtain the desired product (12.0 g).

Infrared absorption spectrum (cm$^{-1}$, Nujol): 1780
NMR spectrum (δ, D$_2$O-acetone-d$_6$): 1.9–2.4(m), 3.50(8H, m), 3.70(3H, s), 4.16(1H, d, J=15 Hz), 4.54(1H, d, J=15 Hz), 5.24(2H, m), 5.78(1H, d, J=5 Hz), 6.87(2H, d, J=10 Hz), 7.33(2H, d, J=10 Hz).

EXPERIMENT 13

7β-Formamido-3-(4-carbamoyl-1-quinuclidinio)methyl-3-cephem-4-carboxylate

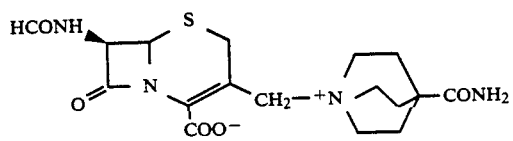

TABLE 2

List of Physical Properties

| Experiment No. | Infrared Absorption Spectrum (cm$^{-1}$, Nujol) | NMR SPECTRUM (δ) |
|---|---|---|
| 2 | 1770 | D$_2$O:2.30(6H, m), 3.2–5.0(m), 5.39(1H, d, J=6Hz), 5.89(1H, d, J=6Hz), 8.35(1H, s) |
| 3 | 1760 | D$_2$O–Acetone-d$_6$:2.10(6H, m), 3.0 4.0(m), 4.60(1H, d, J=6Hz), 4.70(1H, d, J=6Hz), 4.85(1H, d, J=14Hz), 7.10–7.60(15H, m) |
| 4 | 1775 | D$_2$O–Acetone-d$_6$:2.15(6H, m), 3.0–4.4(m), 3.80(2H, s), 4.81(1H, d, J=13Hz), 5.16(1H, d, J=6Hz), 5.63(1H, d, J=6Hz), 6.80–6.95(2H, m), 7.20(1H, m) |
| 5,6,7 | 1780 | D$_2$O:2.30(6H, m), 3.3–4.9(m), 5.31(1H, d, J=6Hz), 5.53(1H, d, J=6Hz) |
| 8 | 1780 | D$_2$O–Acetone-d$_6$:2.15(6H, m), 3.2–4.4(m), 4.95(2H, br.s), 1.46(9H, s), 4.78(1H, d, J=15Hz) |
| 9 | 1780 | D$_2$O:1.60(9H, s), 2.40(6H, m), 3.2–4.4(m), 4.71(1H, d, J=15Hz), 5.45(1H, d, J=6Hz), 5.74(1H, d, J=6Hz) |
| 10 | 1760 | D$_2$O:2.50(6H, m), 3.2–5.0(m), 5.32(1H, d, J=6Hz), 5.41(1H, d, J=6 Hz) |
| 11 | 1780 | D$_2$O–Acetone-d$_6$:2.16(m), 3.1–3.9(m), 3.59(2H, s), 3.75(3H, s), 4.22(1H, d, J=14Hz) 4.57(1H, d, J=14Hz), 5.24(3H, m), 5.73(1H, q, J=5Hz, 10Hz), 6.92(2H, d, J=10Hz), 7.21(5H, s), 7.39(2H, d, J=10 Hz), 8.69(1H, d, J=10Hz) |

The compound (11.8 g) obtained in the preceding Experiment 12 was dissolved in ice-cooled formic acid (50 ml), followed by stirring for 10 hours at room temperature. The reaction solution was subjected to filtration, and the filtrate was added dropwise into acetone (100 ml). To the resulting solution was added dropwise further diisopropyl ether (200 ml). The formed precipitate was collected by filtration, followed by washing with acetone. The precipitate was dissolved in dimethyl formamide (30 ml). The solution was added dropwise in acetone (150 ml). The formed precipitate was collected by filtration, followed by washing with acetone and diisopropyl ether respectively. Thereafter, the solid was dried under a reduced pressure to obtain the desired product (6.66 g).

Infrared absorption spectrum (cm$^{-1}$, Nujol): 1770
NMR spectrum (δ, D$_2$O): 2.30(6H, m), 3.2-5.0(m), 5.39(1H, d, J=6 Hz), 5.89(1H, d, J=6 Hz), 8.35(1H, s).

EXAMPLE 18

7β-[(Z)-2-(5-Amino-1,2,4-thiadiazol-3-yl)-2-methoxyiminoacetamido]-3-(4-carbamoyl-1-quinuclidinio)-methyl-3-cephem-4-carboxylate

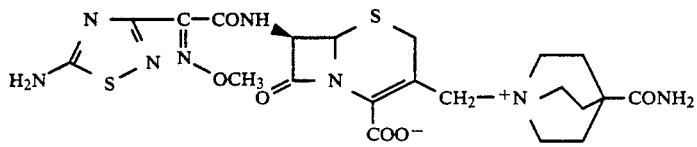

A mixture consisting of 2-(5-amino-1,2,4-thiadizaol-3-yl)-(Z)-2-methoxyiminoacetic acid (46 mg), 1-hydroxy-1H-benzotriazole hydrate (35 mg), N, N'-dicyclohexylcarbodiimide (52 mg), and N, N-dimethylformamide (1 ml) was stirred at room temperature for 3 hours, then the mixture was filtered, and the filtrate was cooled to 0° C. The resulting solution was added to an ice-cooled solution of 7β-amino-3-(4-carbamoyl-1-quinuclidinio)-methyl-3-cephem-4-carboxylic acid hydrochloride (100 mg), N, N-dimethylformamide (2 ml), and N, N-dimethylaniline (72 μl). After stirring the mixed solution at room temperature for 14 hours, the reaction mixture was filtered, and the filtrate was dropped into diethyl ether (100 ml), while stirring the mixture. The deposited precipitate was filtered out and washed with diethyl ether. To the washed precipitate was added water (10 ml), and insoluble matter was filtered off. The resulting filtrate was purified with reversed phase silica gel column chromatography to obtain the desired product (3 mg).

Infrared absorption spectrum (cm$^{-1}$, Nujol): 1775
NMR spectrum (δ, D$_2$O): 2.30(6H, m), 3.1-4.0(m), 4.16(3H, s), 5.43(1H, d, J=6 Hz), 5.97(1H, d, J=6 Hz).

EXAMPLE 19

7β-[(Z)-2-(5-Amino-1,2,4-thiadiazol-3-yl)-2-methoxyiminoacetamido]-3-(4-carbamoyl-1-quinuclidinio)-methyl-3-cephem-4-carboxylate

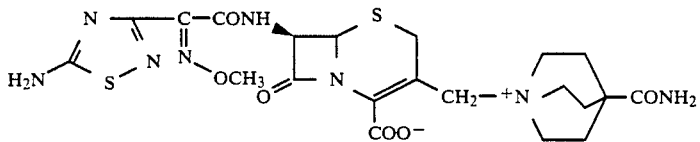

7β-Amino-3-(4-carbamoyl-1-quinuclidinio)methyl-3-cephem-4-carboxylic acid hydrochloride (2 g) was dissolved in acetonitrile-water (1:1) mixed solution (40 ml), and triethylamine (2.08 ml) was added to the solution. The resulting solution was cooled with ice and 2-(5-amino-1,2,4-thiadiazol-3-yl)-(Z)-2-methoxyiminoacetyl-chloride (2.55 g) was added thereto, and the mixture was stirred for 50 minutes. The reaction solution was added to ethanol (200 ml), the deposited solid was filtered, and the solid was washed with ethanol and isopropyl ether, whereby the desired product (450 mg) was obtained.

Infrared absorption spectrum as well as NMR spectrum of the product coincided with those of Example 18.

The compounds of the following Examples 20-28 were synthesized in the same manner as those of Examples 18 and 19.

TABLE 3

| Example | n | Y | R$_1$ | R$_2$ | Infrared Absorption Spectrum (cm$^{-1}$ Nujol) | NMR SPECTRUM (δ, D$_2$O) |
|---|---|---|---|---|---|---|
| 20 | 2 | CH | —CH$_3$ | —CONH$_2$ | 1770 | 2.30(6H, m), 3.30-4.00(m), 4.10(3H, s), 5.45(1H, d, J=6Hz), 5.97(1H, d, J=6Hz), 7.12(1H, s) |
| 21 | 2 | N | —CH$_3$ | —OH | 1765 | 2.20(6H, m), 3.30-4.00(m), 4.18(3H, s), 5.43(1H, d, J=6Hz), 5.97(1H, d, J=6Hz) |
| 22 | 2 | CH | —CH$_3$ | —CH$_2$OH | 1770 | 1.96(6H, m), 3.20-4.00(m), 4.12(3H, s), 5.47(1H, d, J=6Hz), 5.97(1H, d, J=6Hz), 7.15(1H, s) |
| 23 | 2 | CH | —CH$_2$C≡CH | —CONH$_2$ | 1765 | 2.24(6H, m), 3.20-4.20(m), 5.47(1H, d, J=6Hz), 5.99(1H, d, J=6Hz), 7.19(1H, s) |
| 24 | 2 | CH | —CH$_2$CONH$_2$ | —CONH$_2$ | 1770 | 2.30(6H, m), 3.30-4.20(m), 5.48(1H, d, J=6Hz), 6.00(1H, d, J=6Hz), 7.22(1H, s) |
| 25 | 2 | N | —C$_2$H$_5$ | —CONH$_2$ | 1770 | 1.45(3H, t, J=8Hz), 2.30(6H, m), 3.20-4.20(m), 4.46(2H, q, J=8Hz), 5.46(1H, d, J=6Hz), 6.00(1H, d, J=6Hz) |
| 26 | 2 | N | —CH$_2$COOH | —CONH$_2$ | 1765 | 2.30(6H, m), 3.20-4.30(m), 5.44(1H, d, J=5Hz), 6.00(1H, d, J=5Hz) |
| 27 | 1 | N | —CH$_3$ | —OH | 1775 | 2.32(4H, m), 3.30-4.00(m), 4.18(3H, s), 5.43(1H, d, J=6Hz), 5.98(1H, d, J=6Hz) |
| 28 | 1 | CH | —CH$_3$ | —OH | 1765 | 2.30(4H, m), 3.20-4.40(m), 4.08(3H, s), 5.43(1H, d, J=6Hz), 5.94(1H, d, J=6Hz), 7.09(1H, s) |

TABLE 4

Effects of the Invention
Antibacterial Activities

| Sample compound | Test bacterium MIC (μg/ml) | | | | | | |
|---|---|---|---|---|---|---|---|
| | *Staphylococcus aureus* 209-P | *Staphylococcus aureus* E31106* | *Escherichia coli* NIHJ | *Pseudomonas aeruginosa* EP-01 | *Serratia marcescens* ES-75 | *Pseudomonas maltophilia* E04004 | *Citrobacter freundii* EC-34* |
| Example | | | | | | | |
| 1 | 0.8 | 100 | 0.05 | 1.56 | 0.1 | 25 | 0.1 |
| 2 | 0.8 | 50 | 0.1 | 0.8 | 0.2 | 12.5 | 0.1 |
| 3 | 0.8 | 100 | 0.05 | 1.56 | 0.1 | 6.25 | 0.1 |
| 4 | 1.56 | 25 | 0.1 | 0.8 | 0.2 | 6.25 | 0.1 |
| 5 | 1.56 | 100 | 0.05 | 1.56 | 0.05 | 12.5 | 0.1 |
| 6 | 3.13 | 25 | 0.1 | 0.4 | 0.2 | 3.13 | 0.1 |
| 14 | 1.56 | 50 | 0.1 | 0.8 | 0.2 | 3.13 | 0.1 |
| 15 | 0.8 | 50 | 0.05 | 0.8 | 0.2 | 1.56 | 0.05 |

*β-Lactamase producing bacteria.

What is claimed is:

1. A cephem derivative represented by the formula:

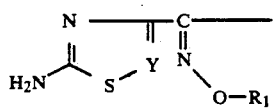

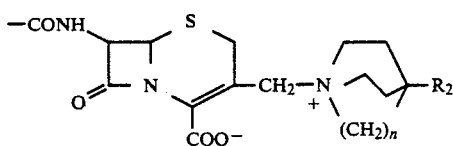

wherein n is 1 or 2, Y is CH, $R_1$ is lower alkyl, lower alkenyl, lower alkynyl or a carboxyl-substituted, a carbamoyl-substituted or a cyclopropyl-substituted lower alkyl group, and $R_2$ is hydroxyl, hydroxy-substituted lower alkyl or carbamoyl, or a pharmaceutically acceptable salt thereof.

2. An antibacterial composition comprising a compound represented by the formula:

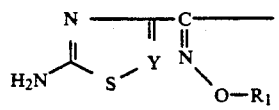

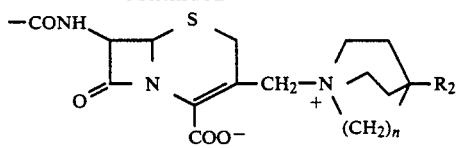

wherein n is 1 or 2, Y is CH, $R_1$ is lower alkyl, lower alkenyl, lower alkynyl or a carboxyl-substituted, a carbamoyl-substituted or a cyclopropyl-substituted lower alkyl group, and $R_2$ is hydroxyl, hydroxy-substituted lower alkyl or carbamoyl, or a pharmaceutically acceptable salt thereof, and a pharmaceutically acceptable carrier therefor.

3. The compound as claimed in claim 1, wherein $R_2$ is hydroxyl.

4. The compound as claimed in claim 1, wherein $R_2$ is hydroxy-substituted lower alkyl.

5. The compound as claimed in claim 1, wherein $R_2$ is carbamoyl.

6. The compound as claimed in claim 1, wherein $R_1$ is lower alkyl.

7. The compound as claimed in claim 1, wherein $R_1$ is methyl or ethyl and $R_2$ is hydroxyl or carbamoyl.

8. The compound as claimed in claim 1, which is 7β-[(Z)-2-(2-aminothiazol-4-yl)-2-methoxyiminoacetamido]-3-(4-hydroxy-1,4-methylene-1-piperidinio)methyl-3-cephem-4-carboxylate represented by the following formula:

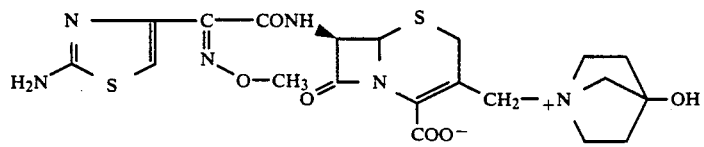

or a pharmaceutically acceptable salt thereof.

9. The compound as claimed in claim 1, which is 7β-[(Z)-2-(2-aminothiazol-4-yl)-2-methoxyiminoacetamido]-3-(4-hydroxy-1-quinuclidinio)methyl-3-cephem-4-carboxylate represented by the following formula:

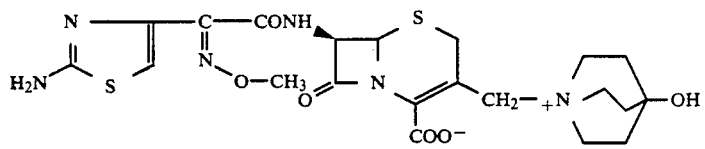
or a pharmaceutically acceptable salt thereof.
10. The compound as claimed in claim 1, which is 7β-[(Z)-2-(2-aminothiazol-4-yl)-2-methoxyiminoacetamido]-3-(4-carbamoyl-1-quinuclidinio)-methyl-3-cephem-4-carboxylate represented by the following formula:
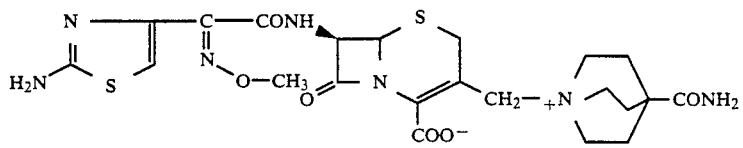
or a pharmaceutically acceptable salt thereof.
* * * * *